(12) United States Patent
Chakeres

(10) Patent No.: US 6,533,794 B2
(45) Date of Patent: Mar. 18, 2003

(54) SIMPLIFIED STEREOTACTIC APPARATUS AND METHODS

(75) Inventor: Donald W. Chakeres, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 09/838,075

(22) Filed: Apr. 19, 2001

(65) Prior Publication Data

US 2002/0156369 A1 Oct. 24, 2002

(51) Int. Cl.⁷ .............................................. A61B 19/00
(52) U.S. Cl. ....................... 606/130; 600/429
(58) Field of Search ................. 606/130; 600/429, 600/417, 427; 604/116

(56) References Cited

U.S. PATENT DOCUMENTS

| | | | |
|---|---|---|---|
| 4,551,678 A | 11/1985 | Morgan et al. | 324/300 |
| 4,583,538 A | 4/1986 | Onik et al. | 128/303 |
| 4,608,977 A * | 9/1986 | Brown | 128/303 |
| 4,618,978 A | 10/1986 | Cosman | 378/164 |
| 4,638,798 A | 1/1987 | Shelden et al. | 606/130 |
| 4,722,336 A | 2/1988 | Kim et al. | 128/303 |
| 4,750,487 A | 6/1988 | Zanetti | 606/130 |
| 5,053,042 A | 10/1991 | Bidwell | 606/130 |
| 5,142,559 A | 8/1992 | Wielopolski et al. | 378/205 |
| 5,147,372 A | 9/1992 | Nymark et al. | 606/130 |
| 5,201,742 A * | 4/1993 | Hasson | 606/130 |
| 5,309,913 A | 5/1994 | Kormos et al. | 600/429 |
| 5,383,454 A | 1/1995 | Bucholz | 600/429 |
| 5,426,685 A | 6/1995 | Pellegrino et al. | 378/87 |
| 5,437,280 A | 8/1995 | Hussman | 128/653.2 |
| 5,447,154 A | 9/1995 | Cinquin et al. | 128/653.1 |
| 5,499,989 A | 3/1996 | LaBash | 606/130 |
| 5,628,315 A | 5/1997 | Vilsmeier et al. | 128/653.1 |
| 5,678,549 A | 10/1997 | Heywang-Koebrunner et al. | 128/653.5 |
| 5,690,108 A | 11/1997 | Chakeres | 128/653.1 |
| 5,830,219 A | 11/1998 | Bird et al. | 606/130 |
| 5,913,863 A | 6/1999 | Fischer et al. | 606/130 |
| 5,961,456 A * | 10/1999 | Gildenberg | 600/429 |
| 5,971,998 A | 10/1999 | Russell et al. | 606/130 |
| 6,132,437 A * | 10/2000 | Omurtag et al. | 606/130 |
| 6,159,221 A * | 12/2000 | Chakeres | 606/130 |
| 6,261,299 B1 * | 7/2001 | Chakeres | 606/130 |
| 6,374,135 B1 * | 4/2002 | Bucholz | 600/427 |
| 6,406,482 B1 * | 6/2002 | Chakeres | 606/130 |

OTHER PUBLICATIONS

Orel et al., Staging of Suspected Breast Cancer: Effect of MR Imaging and MR-guided Biopsy, Radiology 1995; 196:115–122.

Stelling, Breast Cancer Staging with Contrast Material-Enhanced MR Imaging: Should it Change Patient Treatment?, Radiology 1995; 196:16–18.

Mumtaz et al., Laster Therapy for Breast Cancer: MR Imaging and Histophathologic Correclation, Radiology 1996; 200: 651–658.

Orel et al., MR Imaging–Guided Localization and Biopsy of Breast Lesions: Initial Experience, Radiology 1994: 193: 97–102.

* cited by examiner

Primary Examiner—Henry C. Yuen
Assistant Examiner—Frederick Nicolas
(74) Attorney, Agent, or Firm—Standley & Gilcrest LLP

(57) ABSTRACT

The present invention includes a stereotactic system and a method of use for determining vectors involving no electronic components. The stereotactic system comprises a lower plane device and an upper plane device, each having a pair of non-parallel image-conspicuous lines. The system can be used with magnetic resonance imagining (MRI), computed tomography (CT), plain film, radioscopy or fluoroscopy. The relationship of the lines enables a medical practitioner to accurately, directly, and easily determine the vector along which a medical device should be advanced to reach a target within the patient's body using a minimized number of images. As an option, the system may include an additional disposable lower plane device having a pair of non-parallel image-conspicuous lines adapted to determine a skin entry point on the patient for the medical device.

19 Claims, 13 Drawing Sheets

SIMPLIFIED STEREOTACTIC APPARATUS AND METHODS

TECHNICAL FIELD OF THE INVENTION

This invention relates generally to apparatus and methods useful in scientific research and interventional medicine, and useful in the visualization and analysis of organic tissues and bodies; and to research into the cause and symptoms of disease, its diagnosis and treatment. The invention particularly concerns apparatus which may be advantageously utilized by a researcher, physician or health care professional, in conjunction with types of medical imaging equipment, such as computed tomography (CT) imaging equipment or magnetic resonance (MR) imaging equipment, plain film, radioscopy or fluoroscopy. The invention may be utilized to conveniently and accurately aid in timely (real time), manually, truly, and physically accomplishing the steps of locating, vectoring, and inserting an object such as a probe or other needle-like medical device at, toward, and in a patient's targeted anatomic feature.

BACKGROUND OF THE INVENTION

This invention relates to a stereotactic device for use with imaging apparatus, such as magnetic resonance imaging ("MRI"), CT, radioscopy or fluoroscopic apparatus, useful in the visualization and analysis of organic tissues and bodies, and to research into the cause and symptoms of disease, its diagnosis and treatment.

Many stereotactic devices for imaging are currently available. Despite the incredible power of many existing imaging technologies, surprisingly few procedures are actually done using these technologies in a routine clinical setting using any type of stereotactic assistance. There are several reasons for the lack of general acceptance of these devices in existing markets.

Most of these systems are expensive. Normally this expense cannot be justified in terms of usage or benefit for the large capital investment required. Physicians and hospitals are generally not prepared in today's economic climate to make a large investment for a system that may only be used intermittently and may become quickly outdated.

Most existing systems are electronic and use optical and computer interfaces. The majority of these systems do not function in a real-time setting, but rather use special post-processed acquired image information. This information is then used to direct the procedure at a different time and place.

Many of the systems are vendor proprietary or dependent, so it is possible that only a few units may be able to use a specific technology. Though these systems claim to have very high real-space accuracy, in reality they have only limited real-space correlation since there is no live (real-time) imaging to confirm the progress of the procedure.

Most stereotactic units are complex and have multiple components. Some of the systems envelop the patient, such as through the use of head frames bolted directly to the skull. If there is any change in the components of such a rigid system at the time and place of the actual intervention, the previously obtained information that forms the basis for the intervention is no longer valid.

These systems also rely on gathering many images to direct the operation, rather than needing only a few. Because of this, the process can be very slow, since a large amount of data needs to be acquired to direct the process.

A number of existing stereotactic systems utilize fiducials that are placed on the patient or the stereotactic frame. These are image-conspicuous markers that are seen in the image space and in real-space. Utilizing this information, the virtual reality space depicted on the images is then fused with the real-space.

There are a number of devices that attach directly to the scanner, but these are generally cumbersome and have not been used extensively.

There are also a few systems that use very limited vector trajectories (of only a few angles). These are of little value since the limited number of approaches they provide to the target may not be enough to address the complicated anatomy, therapeutic devices, and goals of a variety of procedures.

Currently there are a number of rapid CT or MRI data acquisition systems available, but they have the disadvantages of being proprietary and of exposing the patient and operator to increased radiation dosage. These CT systems are analogous to fluoroscopy.

There are a few combined CT and fluoroscopic stereotactic systems. These have the potential to be very versatile, but they are complex proprietary systems. There are also a number of open magnet designs, but these are limited by vendor design. Critical information used to direct the procedure or intervention is based on artifacts from the needle or probe rather than on accurate real-time real-space information. The inherent imaging problems created by these artifacts limit the accuracy of these devices. In general the image quality of the fast imaging systems is not as good as routine imaging techniques.

FIG. 1 is a schematic of an enveloping frame that is used for head stereotactic systems of the prior art. The vertical lines 1 of the box represent the vertical struts, the horizontal lines 2 are crossing members used to define the section plane, the angled lines 3 represent cross-members, and the sphere 4 is the target. This frame is bolted or rigidly fixed to the patient and then imaged with many sections. The information gathered is used at a later time and place. Without real-time real-space confirmation during the intervention, there is no absolute confirmation that the previously determined plan is actually being correctly implemented.

FIG. 2 is a schematic of an image obtained from such a fixed frame rigid system. The vertical members 1 are seen at the corners of the square. The cross-members 3 are used to define the slice location and the target 4. There is no intuitive information that an operator can use to confirm that the information is accurate. Typically, a second system is used to actually execute the procedure at a later time with no real-time real-space confirmation of the previously obtained plan.

FIG. 3 shows an example of an MRI image 5 showing the use of a fixed frame stereotactic unit used for head imaging. The head 6 appears in the center of the image, with the target labeled in the left temporal bone. Also visible are the rods 7 (such as horizontal, vertical and cross-members 1, 2 and 3 shown in FIG. 2) surrounding the skull of the patient as a fixed device. The information is acquired by taking multiple images that must be post-processed.

There are a number of limitations to this type of device. The constituent support tubes are necessarily relatively large (in order to support the static arrangement), and thus cause a certain degree of inherent error in the system. The image shown is a single image that provides no real-time information that an operator might use during an image-monitored procedure. Also, a further error factor arises because the tubes are relatively distant from the target site, and the image itself is not without distortion, making the system distortion sensitive. Also, if the subject is moved then the system cannot be readily realigned.

A number of computer-based virtual reality systems' disadvantages have been mentioned. The most important of these is that they provide no real-time confirmation at the actual time of intervention. All of these systems use specially acquired post-processed images that assume the virtual reality of the previously obtained imaging information and the true reality at the time of the actual intervention are identical. These systems are expensive, large, and can only be used in select locations.

There remain problems associated with fast, open, and combined technology systems. All are expensive, vendor specific and, as such, are limited to only a few sites. They are such complicated systems that any minor problem can render them useless, such as if the batteries on an LED were to stop working. They have limited real-space accuracy since they have problems with partial volume averaging and other imaging artifacts. Using these systems it may be difficult to track more than one device being used at a time.

Accordingly, the criteria for an improved stereotactic device include:

1. Accuracy in the form of mm level control and live image confirmation.
2. Ability to make rapid adjustments (preferably by remote control), and the use of a single image.
3. Flexibility in the form of multiple dimension adjustability, and the accommodation of a wide variety of probes.
4. Intuitive use through clear, non-computer-generated interpretation of electronic image information.
5. Simple construction; a device that may be compact enough to fix the imager on the patient and inexpensively constructed, and may be of disposable materials.
6. Applicability independent of site and imaging device.

Accordingly, there remains a need for relatively inexpensive stereotactic devices that may be used with a wide variety of imaging systems for the performance of varied procedures, and that may be used with any number of invasive devices and techniques.

SUMMARY OF THE INVENTION

The present invention defines stereotactic vectors requiring no electronic components. The present invention includes a stereotactic device for cross-sectional imaging.

The theory upon which the present invention is based is that two points define a line. The line is used as the vector that an appropriate medical device is advanced along to contact a target located inside the patient. With this device, a target may be contacted by a medical device (e.g. probe) using a minimum of two or three images.

The two points defining the vector outside of the patient's body are determined using two sets of non-parallel image-conspicuous lines. The sets of non-parallel image-conspicuous lines may be derived from a number of standard geometric shapes.

The following paragraphs describe the geometric shapes preferred in development of an image-conspicuous pattern used by a stereotactic device of the present invention. It should be duly noted that other geometric shapes may provide similar results and that the examples given below are not intended to limit the invention.

FIG. 4 shows a triangle 40 that may provide the basis of design for a stereotactic device in accordance with one embodiment of the present invention. The triangle 40 shown is an isosceles triangle (i.e. two equal sides). However, any triangle may be adapted to perform the functions as described with the isosceles triangle. The triangle 40 has a first side 40a, a second side 40b and a third side 40c. The first side 40a is equal in length to the second side 40b. The first side 40a and the second side 40b are preferably made from an appropriate image-conspicuous material. The third side 40c may be used to align a stereotactic device on the patient by placing the third side parallel to the image plane.

Preferably, spanning the distance between the first side 40a and the second side 40b are span lines 42. The span lines 42 are parallel to the third side 40c. The span lines 42 are preferably equidistant from one another. The span lines 42 are preferably constructed of image-inconspicuous material. Along either the first side 40a or the second side 40b are span numbers 43 indicating the length of corresponding span lines 42. In a preferred triangle, the length of the span lines 42 corresponds to the distance of the span line to the angle defined by the first side 40a and the second side 40b. Alternatively, the distance between the first side 40a and the second side 40b is identified by appropriate markings along either the first side 40a, the second side 40b or both first side 40a and second side 40b. An appropriate marking is one that allows the user to positively identify and locate the distance between the first side 40a and the second side 40b.

Preferably, a set of offset lines 44 spans the distance between the second side 40b and the third side 40c running parallel to the first side 40a. The offset lines 44 are preferably equidistant from one another and preferably constructed from an image-conspicuous material so as to appear on an image. Offset numbers 45 indicate the distance of corresponding offset lines 44 from the first side 40a.

A reference 41 constructed of image-conspicuous material aids the medical professional in interpreting an image taken by providing a mark on said image thereby eliminating confusion about right-left orientation of the pattern on the patient.

A distance between the first side 40a and the second side 40b parallel to the third side 40c shall be referred to as a chord 48. Each chord is a unique length because the first side 40a and the second side 40b are non-parallel. The entry point 47 is defined by a chord 48 and an offset 46. The offset 46 is the distance from the first side 40a to the entry point 47 along a chord 48. Alternatively, the chord 48 may be thought of as a slice location because it indicates the slice that the imaging machine operated upon.

FIG. 5 shows a quadrilateral 50 that may provide the basis of design for one embodiment of the present invention. Quadrilateral 50 has a first side 50a, a second side 50b, a third side 50c and a fourth side 50d. The second side 50b is parallel to the fourth side 50d. The third side 50c forms a right angle with both the second side 50b and the fourth side 50d. The third side 50c is not parallel to the first side 50a. Preferably, the first side 50a and the third side 50c are made from an appropriate image-conspicuous material. The fourth side 50d is used to align the stereotactic device on the patient parallel to the image plane.

Preferably, spanning the distance between the first side 50a and the third side 50c are span lines 52. The span lines 52 are parallel to the second side 50b and the fourth side 50d. The span lines 52 are preferably equidistant from one another. The span lines 52 are preferably constructed of an image-inconspicuous material. Along either the first sdie 50*a* or the third side 50*c* are span numbers 53 indicating the length of corresponding span lines 52. Alternatively, the distance between the first side 50*a* and the third side 50*c* is identified by appropriate markings along either the first side 50*a*, the third side 50*c* or both first side 50*a* and third side 50*c*. An appropriate marking is one that allows the user to positively identify and locate the distance between the first side 50*a* and the third side 50*c*.

Preferably, offset lines 54 span the distance between the second side 50*b* and the fourth side 50*d* parallel to the first side 50*a*. The offset lines 54 are preferably equidistant from one another and constructed of an appropriate image-conspicuous material so as to appear on an image. Offset numbers 55 indicate the distance of corresponding offset lines 54 from the first side 50*a*.

A reference 51 constructed of image-conspicuous material aids the medical professional in interpreting an image taken by providing a mark on said image thereby eliminating confusion about orientation of the pattern on the patient.

A distance between the first side 50*a* and the third side 50*c* parallel to the second side 50*b* and the fourth side 50*d* shall be referred to as a chord 58. Each chord is a unique length because the first side 50*a* and the third side 50*c* are non-parallel. The entry point 57 is defined by a chord 58 and an offset 56. The offset 56 is the distance from the first side 50*a* to the entry point 57 along a chord 58.

FIG. 6 shows a trapezoid 60 that may provide the basis of design for one embodiment of the present invention. Trapezoid 60 has a first side 60*a*, a second side 60*b*, a third side 60*c* and a fourth side 60*d*. The first side 60*a* and the third side 60*c* are parallel. The second side 60*b* and the fourth side 60*d* are not parallel to one another. Preferably, the second side 60*b* and the fourth side 60*d* are of equal length. The second side 60*b* and the fourth side 60*d* are preferably made of an appropriate image-conspicuous material. The first side 60*a* is used to align the stereotactic device on the patient parallel to the image plane.

Preferably, spanning the distance between the second side 60*b* and the fourth side 60*d* are span lines 62. The span lines 62 are parallel to the first side 60*a* and the third side 60*c*. The span lines are preferably equidistant from one another. The span lines 62 are preferably constructed of an image-inconspicuous material. Along either the second side 60*b* or the fourth side 60*d* are span numbers 63 indicating the length of corresponding span lines 62. Alternatively, the distance between the second side 60*b* and the fourth side 60*d* is identified by appropriate markings along either the second side 60*b*, the fourth side 60*d* or both second side 60*b* and fourth side 60*d*. An appropriate marking is one that allows the user to positively identify and locate the distance between the second side 60*b* and the fourth side 60*d*.

Preferably, offset lines 64 span the distance between the first side 60*a* and the third side 60*c* parallel to the second side 60*b*. The offset lines 54 are preferably equidistant from one another and preferably constructed from an image-conspicuous material so as to appear on an image. Offset numbers 65 indicate the distance of corresponding offset lines 64 from the second side 60*b*.

A reference 61 constructed of image-conspicuous material aids the medical professional in interpreting an image taken by providing a mark on said image thereby eliminating confusion about right-left orientation of the pattern on the patient.

A distance between the second side 60*b* and the fourth side 60*d* parallel to the first side 60*a* shall be referred to as a chord 68. Each chord is a unique length because the second side 60*b* and the fourth side 60*d* are non-parallel. The entry point 67 is defined by a chord 68 and an offset 66. The offset 66 is the distance from the second side 60*b* to the entry point 67 along a chord 68.

FIG. 7 shows the relationship of the lines of an image-conspicuous pattern 70 that includes a first image-conspicuous line 71 and a second image-conspicuous line 72. It has already been said that the two lines cannot be parallel to one another for the present invention to operate. In fact, a preferred angle 75 between the first image conspicuous line 71 and the second image-conspicuous line 72 is 53 degrees. If the image-conspicuous pattern 70 were derived from a triangle, then the first image-conspicuous line 71 would intersect the second image-conspicuous line 72. However, if the image-conspicuous pattern were derived from other geometric shapes, the image-conspicuous lines may need to be extended to accurately measure the angle 75. A first extension 73 is drawn from image-conspicuous line 71. A second extension line 74 is drawn from image-conspicuous line 72. The point where the first extension 73 intersects the second extension 74 is referred to as the intersection point 76. Having identified the intersection point 76, angle 75 may be measured.

At an angle of 53 degrees, the device pattern has a unique characteristic. The distance 78 between the first image conspicuous line 71 and the second image-conspicuous line 72 of the pattern measured on an image when the slice symmetrically crosses the pattern (parallel to the base of the triangle, not shown) is equal to the distance 77 between the intersection point 76 and the image plane (not shown). Note that independent of where the image slice crosses the pattern, the distance from the intersection of the two limbs is encoded on the image by the pattern being of an image-conspicuous material. This relationship allows for immediate exact definition of the location of the section plane in real-space on the pattern using only this simple image information.

The device of the present invention is in part based on a unique image pattern that encodes exact dimensional information (e.g., in mm) on each image that is directly related to the identical dimensional positions (e.g., in mm) in real-time and 3D space. This means there is no need for computers or any other type of complex translation of the image information to utilize data in the real-time space of the image system.

The pattern generated by devices of the present invention, in its preferred embodiment, is based on a specific geometric oddity. A triangle formed in a square has this property when the base of the triangle is the base of the square and the apex of the triangle is the midpoint of the top of the square. The triangle formed in this specific situation is a special isosceles triangle of about 53 degrees. The pattern of the preferred inventive device uses the limbs of this triangle. The limbs of the preferred device pattern are made of image-conspicuous materials. A similar geometric relationship between two image-conspicuous limbs can be obtained using a right triangle with a 45-degree apex, but this has a number of functional limitations, therefore the 53-degree design is preferred. When the imaging section plane is parallel to the pattern it produces a set of unique imaging and real-space characteristics. The true distance between the limbs of the device's image-conspicuous pattern as measured on the image is equal to the true distance from the intersection apex of the pattern limbs. There is no need for a computer to tell the operator when this occurs or for complex calculations. The slice location is encoded as a true linear measurement on the image.

The distance from one reference limb of the device's image-conspicuous pattern to a vector line measured on the image can be used to define the same point in real-space on the device.

For instance, when using CT, each limb of the "V" may be made of an image-conspicuous material such as a metal wire. In the case of MRI, tubes (typically non-metallic; plastic) filled with contrast-enhanced fluid may be used as pattern limbs. The pattern may also be drawn directly on the patient, or included on an imager transparent material attached to the patient, such as through the use of adhesives. Examples may include a piece of flexible material, such as Mylar, provided with an adhesive on one side and bearing an image-conspicuous pattern (provided in the form of an attached image-conspicuous object in the shape of the "V", or in the form of a printed design in the shape of the "V" in accordance with the present invention). Another example may be an adhesive strip, similar to an adhesive bandage, and provided with image conspicuous material members attached thereto, or an image-conspicuous "V" pattern printed thereupon.

Thus, one of the fundamental features of the preferred device is that it provides a three-dimensional alignment template that resides at a distance from the identified target point without having the target point located within the space defined by the three-dimensional alignment template. This allows the three-dimensional alignment template to be repositioned and to function accurately even if the tissue or patient has moved.

Preferably each of the above mentioned geometric shapes is adapted with an image-conspicuous means that can assist in identifying the offset of the entry point through that plane. Examples of preferred means include a set of parallel image-conspicuous lines adapted to appear as dots on an image that can be used to accurately measure the offset or as a moveable member adapted with image-conspicuous markers that appear as dots on an image to measure offset.

Generally, devices in accordance with present invention may be accurate to within 1 or 2 units (i.e., mm or less) of the limits of the image resolution. These levels of accuracy may be achieved independent of the section thickness and orientation.

Having fully described the geometric basis for the invention, we shall now discuss the general operation of the invention.

Initially, a skin point localizer is placed on the surface of the skin at a position where it is thought that entry into the body would be advantageous. The skin point localizer is constructed using a geometric shape (explained below). The geometric shape has at least two image-conspicuous lines capable of being captured by the imaging equipment. The skin point localizer is positioned such that the image plane is parallel to the offset line. An image is taken and the target is identified. The two image-conspicuous lines, having been properly oriented prior to imaging, show up on the image as two points. A vector may then be defined by drawing a line from the target through the space between the two points generated by the image-conspicuous material. Measurements are taken from the image such as the distance between the two image-conspicuous points and the distance from one of the points to the intersection of the line with the line that would be formed by connecting the two image conspicuous points. These measurements are the transferred to the skin point localizer. By measuring the distance between the two points the correct chord may be identified. The chord represents the slice location of the imaging device. By measuring the distance from one of the points to the intersection of the line with the line that would be formed by connecting the two image conspicuous points the offset may be identified. The skin point localizer defines a lower plane on the surface of the patient and the point through which an appropriate medical device will enter the patient. The skin point localizer is marked in an appropriate fashion and the patient is sterilzed, if necessary.

Alternatively, the skin point localizer may be a disposable item that is replaced, after marking the skin entry point and sterilizing the area, with a sterilized skin point localizer.

An upper plane apparatus, having at least two image-conspicuous lines, is then affixed onto the patient in such a manner as to capture the vector drawn onto the first image between its image-conspicuous lines. The upper plane apparatus is essentially parallel to the plane defined by the skin point localizer. It is important that the offset line of the lower plane device be parallel to the offset line of the upper plane apparatus. With the offset lines parallel to one another, the next image will enable the practitioner to accurately define and control the vector in three-dimensional space. A second image is then taken. From the second image, measurements similar to those taken from the first image are taken. Preferably, verifying the coordinates of the lower plane's skin point localizer. The vector can be defined in terms of its intersection with the each plane (the first defined by the skin point localizer and the second by the upper plane apparatus) and the desired target. A suitable medical device may then be advanced along the vector so defined. The depth of insertion may additionally be measured from the image and used to ensure that the medical device is advanced the appropriate distance. Preferably, after the medical device has been inserted a short distance (typically a centimeter or two) a next image is taken to verify that the medical device is following the vector and that the alignment is correct so that contact with the target is achieved.

Examples of appropriate image-conspicuous materials include metal wire for computed tomography (CT) imaging equipment or barium paste or a liquid ink for magnetic resonance imaging (MRI) equipment.

In a real-time environment, the visual cues generated by the device-generated image-conspicuous pattern lead the operator to an exact real-time space location without the need of special computer information. The device and methods of the present invention may be used with any diagnostic or clinical imaging device, such as MRI, CT, or fluoroscopy devices. The device and methods of the present invention may also be used with industrial imaging devices in fields even outside of life sciences and medicine.

When an instrument is attached to a pattern device of the present invention, its position may be encoded independent of the slice thickness. Accordingly, partial volume artifact vector errors may be eliminated. The relationship of the instrument to the image may be encoded, a capability not possessed by known prior art devices.

DETAILED DESCRIPTION OF THE PREFERRED EMBODIMENT(S)

In accordance with the foregoing summary of the invention, the following is a detailed description of preferred embodiments of the invention, and is presently considered to be the best mode of the invention as applied.

The device of the present invention may be made of any combination of appropriate materials such as sterile, biocompatible materials (e.g., plastic, wire, tubes, catheters, diaphragms, etc.).

Figure 1:
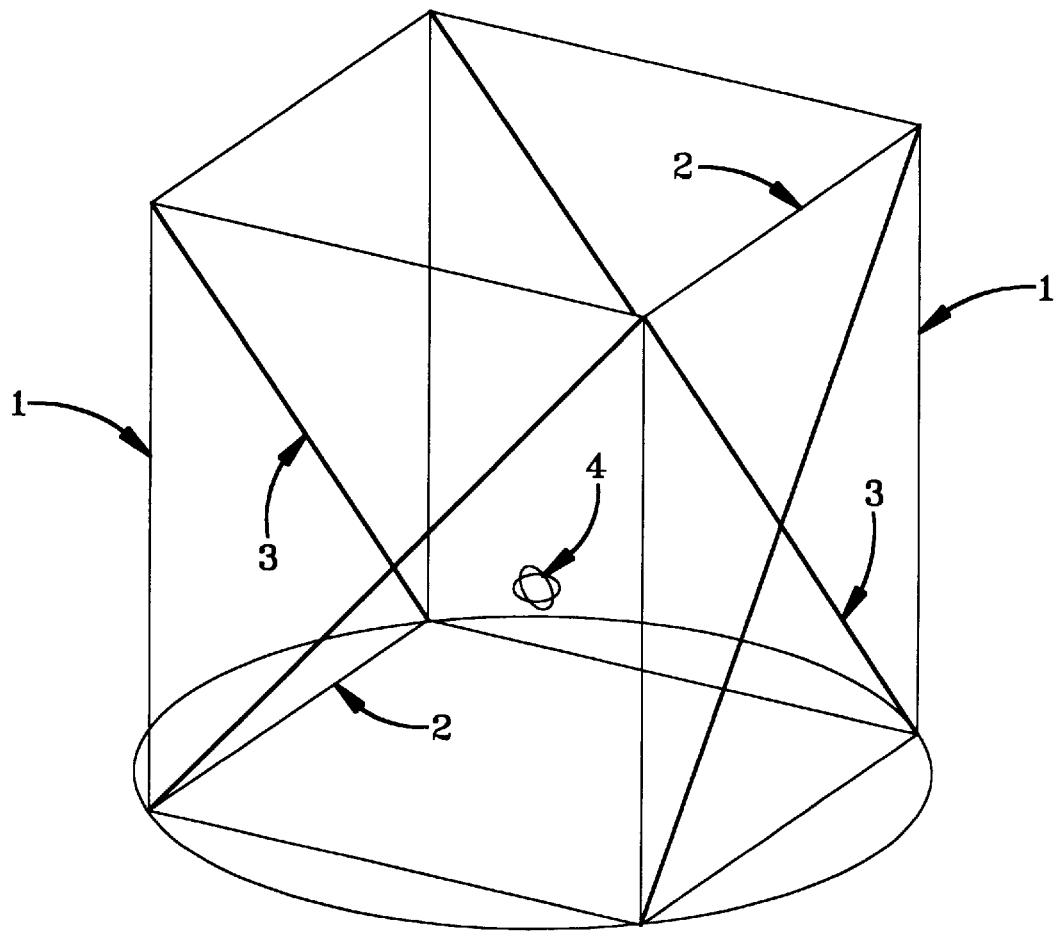
FIG. 1 is a schematic of an enveloping frame that is used for head stereotactic systems of the prior art.
Figure 2:
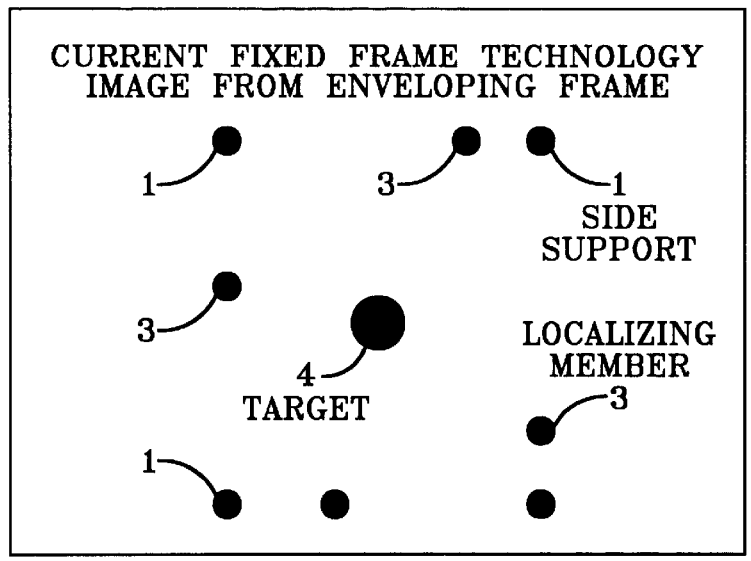
FIG. 2 is a schematic of an image obtained from a fixed frame rigid system in accordance with the prior art.
Figure 3:
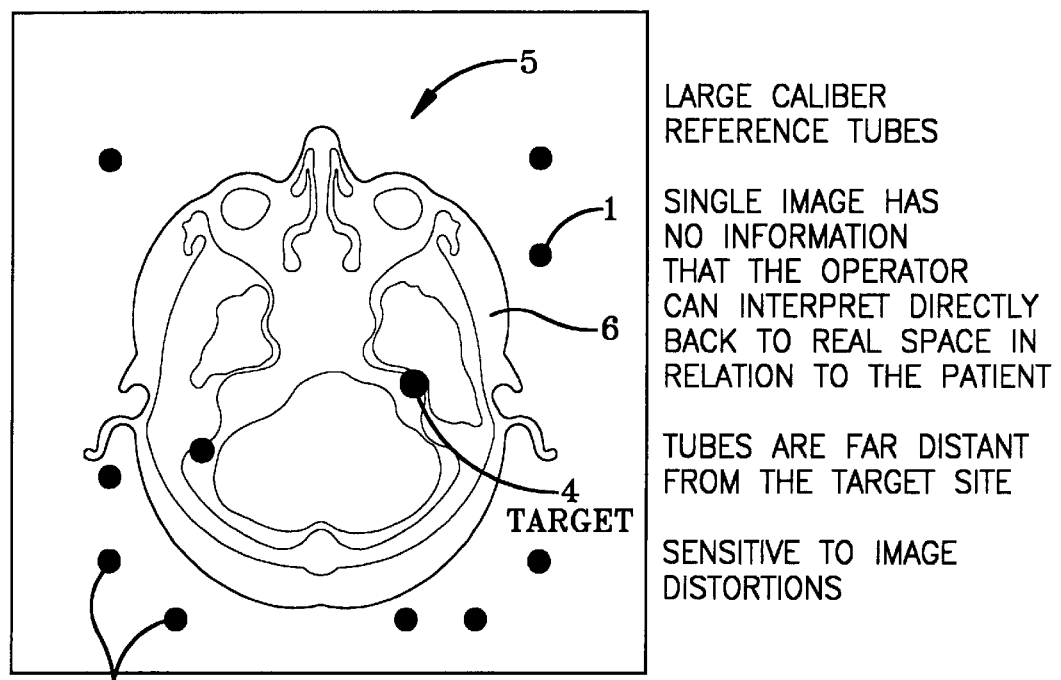
FIG. 3 shows an example of a MRI image showing the use of a fixed frame stereotactic unit used for head imaging in accordance with the prior art.
Figure 4:
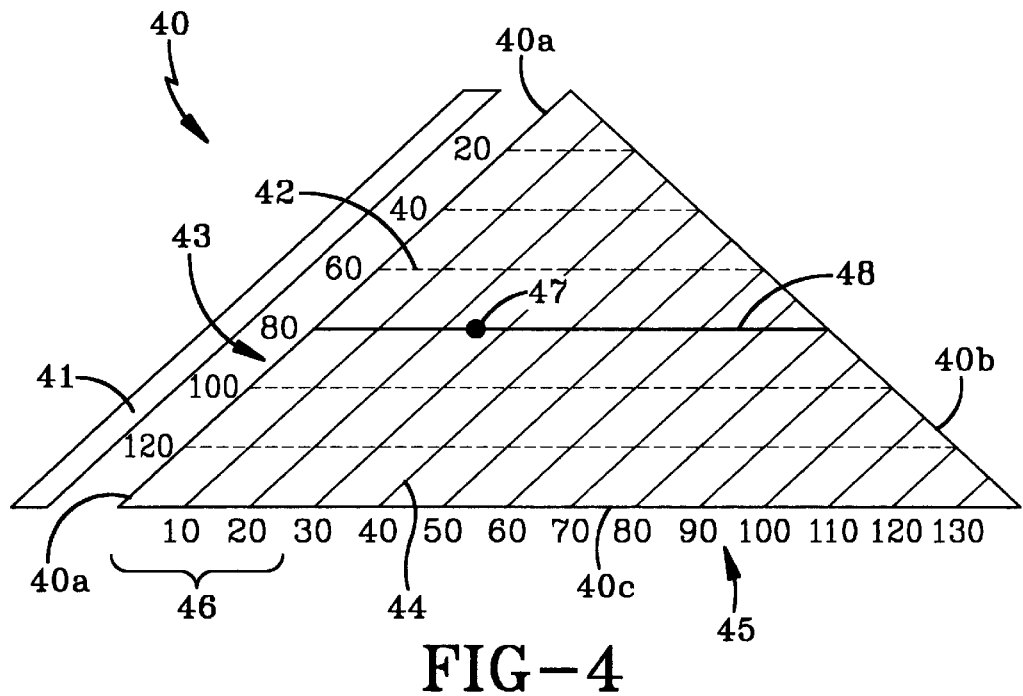
FIG. 4 illustrates the use of a triangle shape in the stereotactic device.
Figure 5:
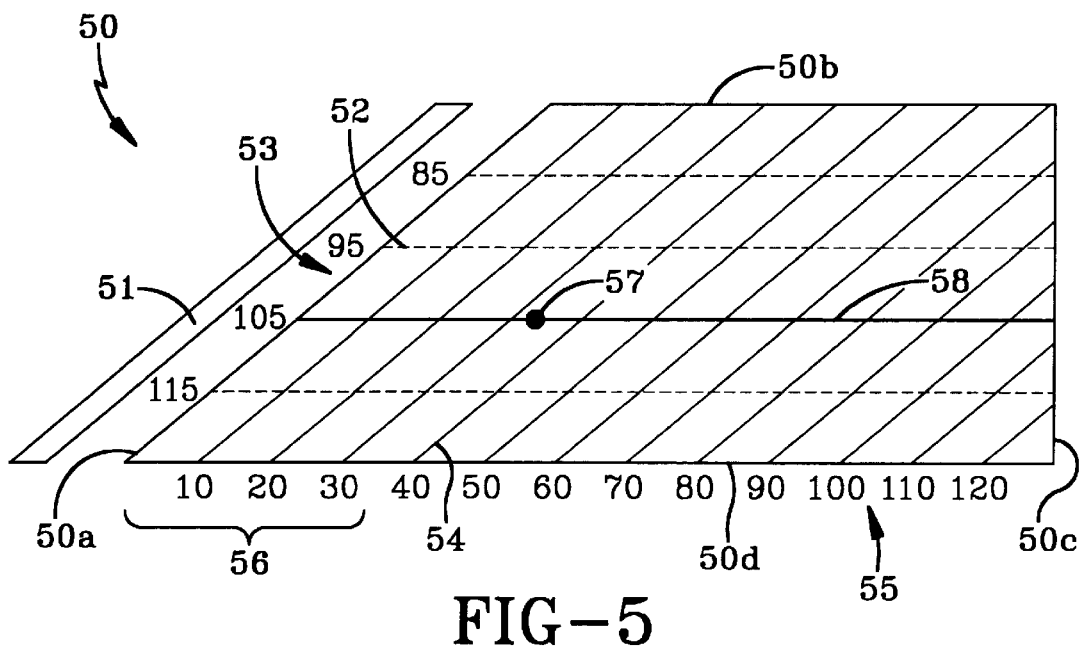
FIG. 5 illustrates the use of a quadrilateral shape in the stereotactic device.
Figure 6:
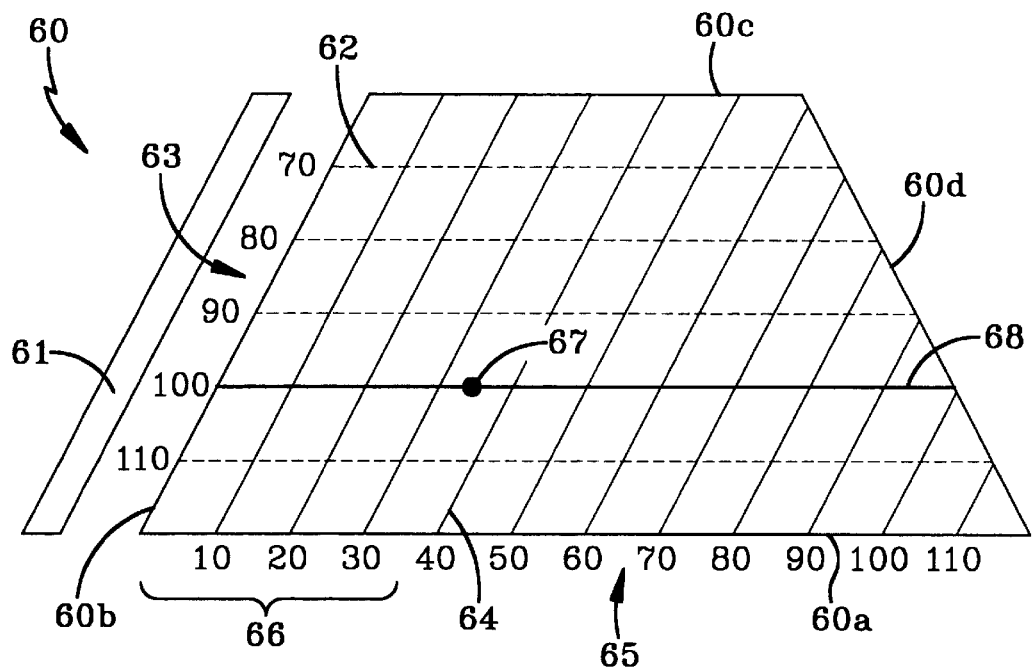
FIG. 6 illustrates the use of a trapezoid shape in the stereotactic device.
Figure 7:
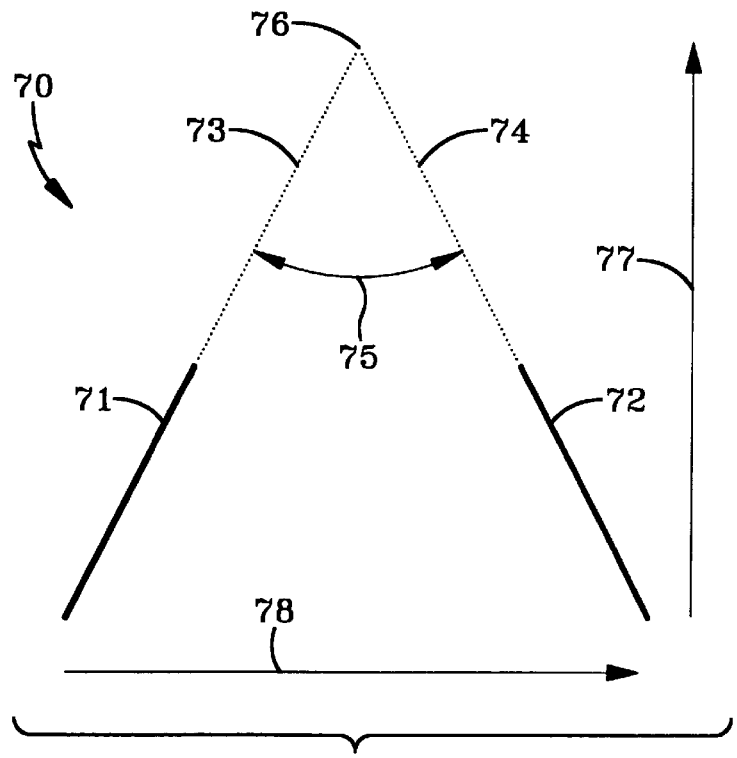
FIG. 7 illustrates the relation of the image-conspicuous lines to one another.
Figure 8:
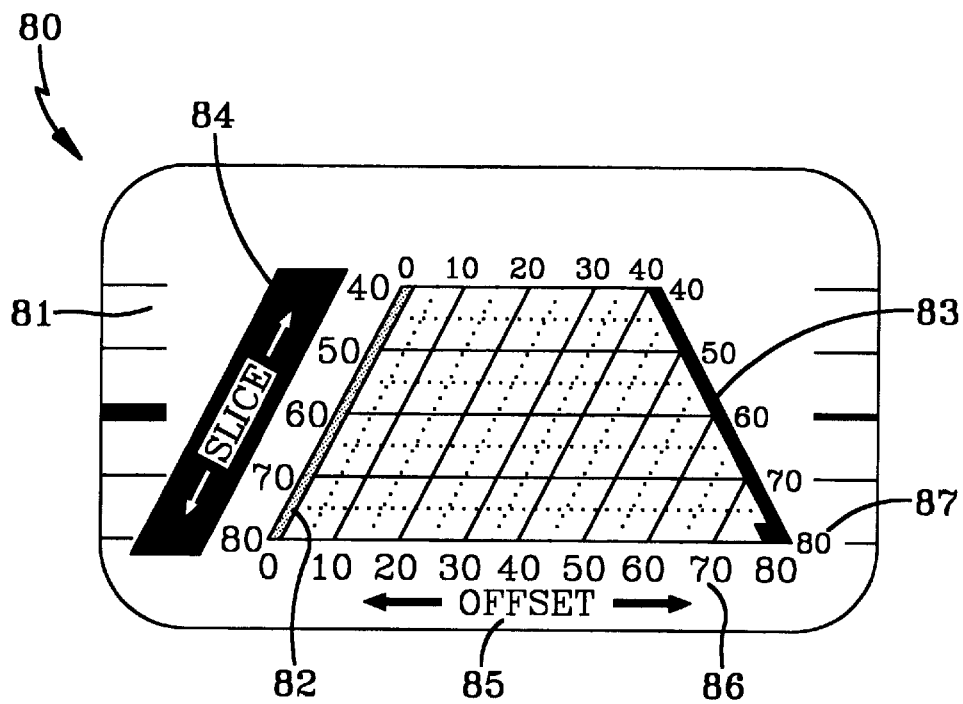
FIG. 8 is a photograph of an optional disposable lower plane device used to identify the skin entry point in accordance with one embodiment of the present invention.

FIG. 8 shows a top view of a disposable lower plane device 80 in accordance with one embodiment of the present invention. The disposable lower plane device may be constructed from any appropriate material including paper and adhesive-backed paper. The disposable lower plane device 80 is comprised of a first image-conspicuous line 82 and a second image-conspicuous line 83. The first line 82 is in non-parallel relationship to the second line 83, preferably the angle between the two lines in 53 degrees. The disposable lower plane device preferably comprises offset calibrations 85 and offset markers 86. The disposable lower plane device 80 additionally preferably comprises image-conspicuous slice orientation marker 84 and slice calibrations 87.

Figure 9:
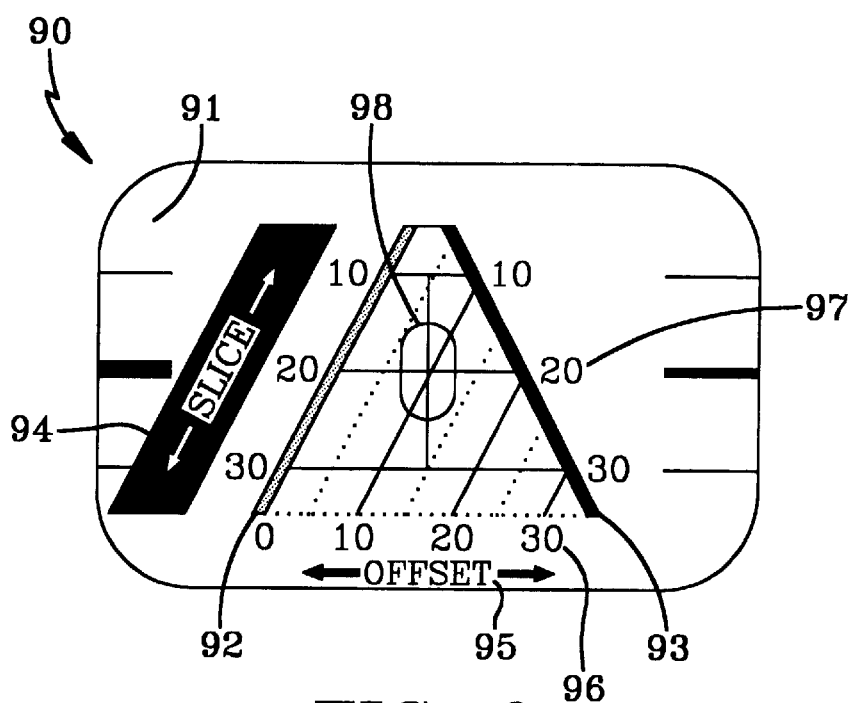
FIG. 9 is a photograph of a lower plane device in accordance with one embodiment of the present invention.

FIG. 9 shows a preferred lower plane device 90. A preferred lower plane device 90 is constructed from an adhesive medical bandage 91. A lower plane device 90 comprises a first image-conspicuous line 92 and a second image-conspicuous line 93. The first line 92 is in non-parallel relationship to the second line 93, preferably the angle between the two line 92, 93 is 53 degrees. The lower plane device 90 preferably comprises offset calibrations 95 and offset markers 96. The lower plane device 90 additionally preferably comprises image-conspicuous slice orientation marker 94 and slice calibrations 97. It is preferred that the lower plane device 90 additionally comprise a hole 98. The hole 98 is preferably located midway between the first image conspicuous line 92 and the second image-conspicuous line 93. The hole 98 is adapted to permit passage of a suitable medical device (not shown).

Figure 10:
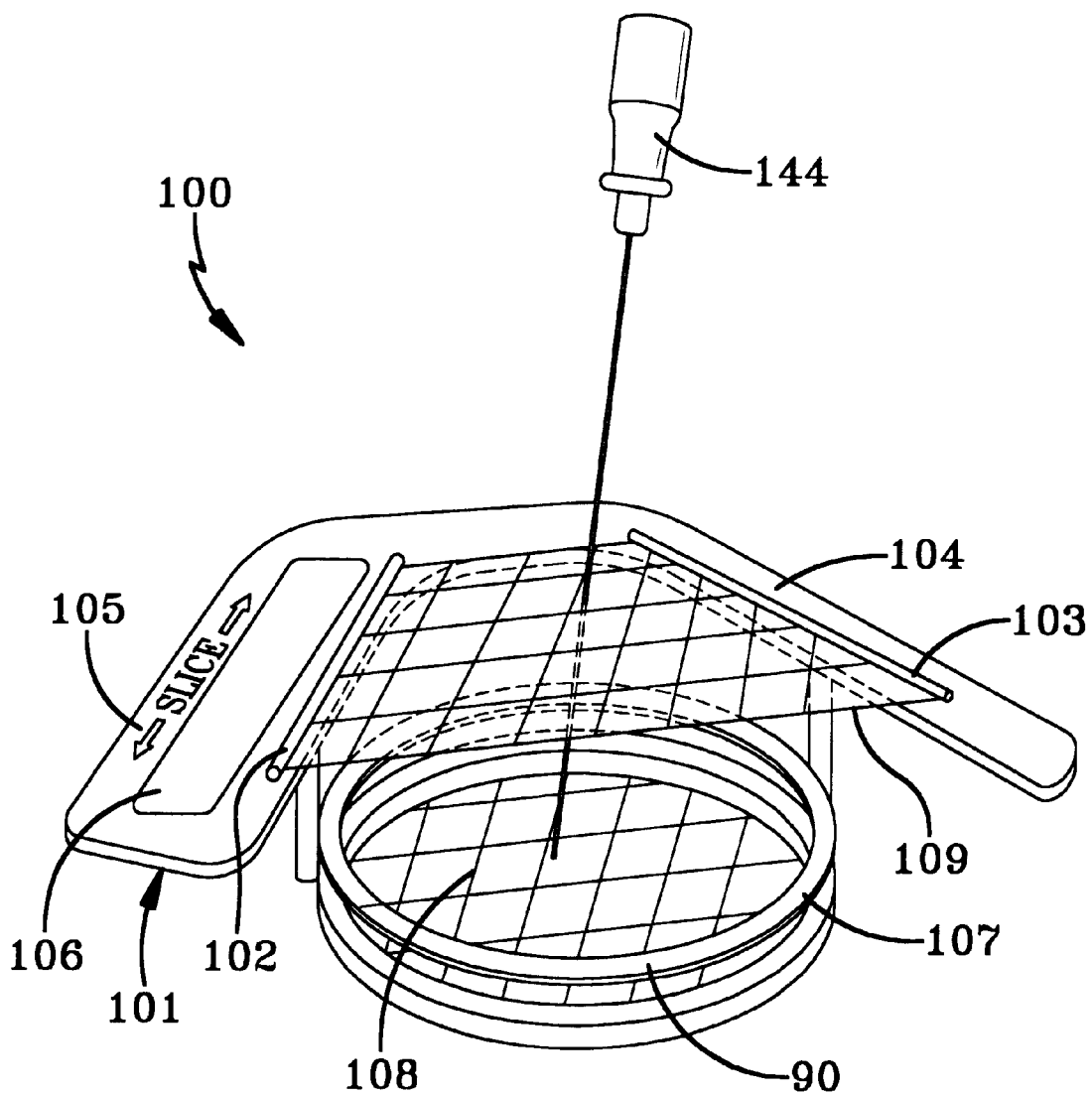
FIG. 10 is a photograph of a stereotactic device that may be used in accordance with one embodiment of the present invention.

FIG. 10 shows a stereotactic system 100 of the present invention in accordance with one embodiment. The stereotactic system 100 is comprised of a lower plane portion 90 (previously described) and an upper plane portion 104. The lower plane portion 90 and the upper plane portion 104 are substantially parallel to one another. The upper plane portion 104 is supported above the lower plane portion 90 by frame 107. A preferred upper plane portion 104 is comprised of a first image-conspicuous line 102 and a second image-conspicuous line 103. The first image-conspicuous line 102 and the second image-conspicuous line 103 are not parallel. It is preferred that the upper plane portion 104 be further comprised of a transparent member 109 capable of being pierced by a suitable medical instrument 144 (shown). Additionally, preferred embodiments further comprise an image-conspicuous orientation marker 105, image-inconspicuous slice location markers 106, and preferably image-conspicuous offset gradations 108.

Alternatively, the transparent member 109 may have predisposed with holes to permit passage of a suitable medical device. The predisposed holes would preferably be equidistant from one another.

Figure 11:
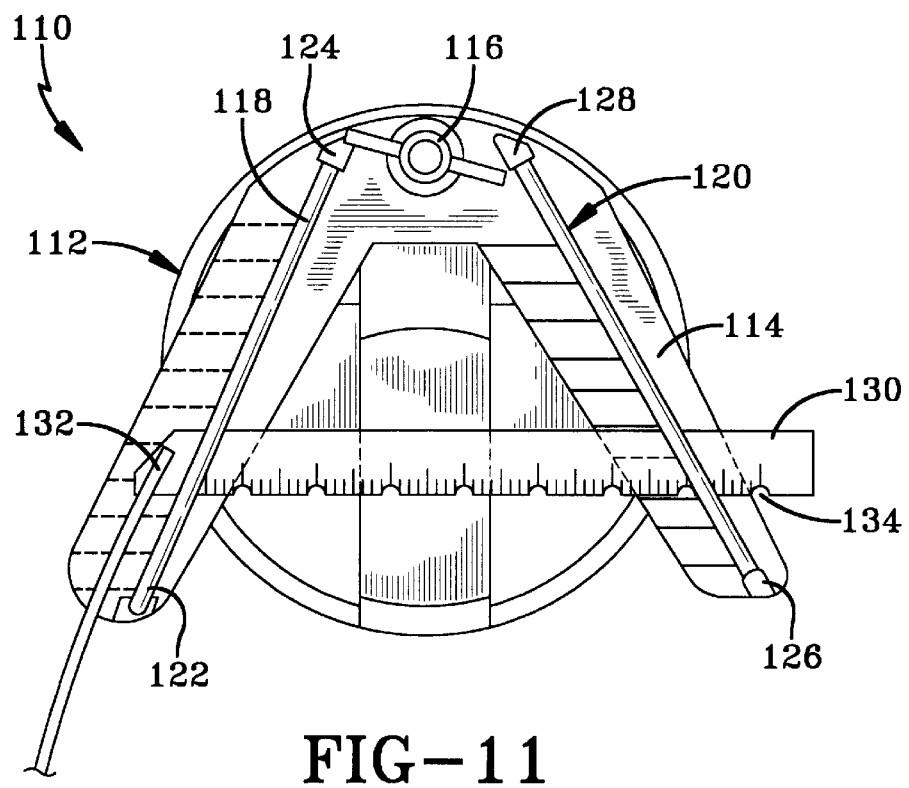
FIG. 11 is a top view of a stereotactic device that may be used in accordance with one embodiment of the present invention.

FIG. 11 shows a top view of an upper plane device 110 in accordance with one embodiment of the present invention. FIG. 11 shows a frame portion 112 supporting an upper plane portion 114. The frame portion defines an upper alignment plane, and has an opening of sufficient size for at least a portion of a medical device or instrument, such as a needle or syringe, to pass. In the embodiment shown in FIG. 11, the frame defines a portion of a circular rim, leaving the entire central area available for penetration. In a preferred embodiment, as shown in FIG. 11, the frame 112 is made of a transparent material, thereby increasing overall visibility. The device shown in FIG. 11 may be useful for such applications as MRI or CT imaging.

The upper plane portion 114 is connected to the upper, planar edge of the frame 112. The upper portion may be connected by any appropriate means, but is shown in the figure to be connected by way of a plastic wing nut 116. It is preferred that the upper plane portion 114 be parallel to the upper alignment plane. The upper plane portion may be of any appropriate shape, having an area of an appropriate size to allow passage of the medical device or instrument. In the preferred embodiment shown in FIG. 11, the upper plane portion 114 has a V-like shape such that the open area designated for instrument passage is maximized.

The upper plane portion 114 contains a pair of image-conspicuous lines, a first line 118 and a second line 120, preferably of equal length and thickness. The lines may be of any appropriate image-conspicuous material, but are preferably composed of tubes containing a sterile, image-conspicuous fluid for MRI imaging or wire with a barium ink or paste or other appropriate coating for CT imaging. The lines are positioned in a plane parallel to the upper plane portion 114, disposed with respect to one another so as to form an angle of appropriate measure. It is preferred that the smaller end of the angle be at the end of the device near the connector 116, and that the angle bisector overlie a line tracing a full diameter of the circular frame so as to be symmetrical with respect to said frame. The first line 118 is connected to the upper plane portion at a first end 122 and a second end 124, the second line 120 also connected at a first end 126 and a second end 128. The upper plane portion 114 or first and second lines 118, 120 may have any appropriate gradations or scales to assist in measurement.

Figure 12:
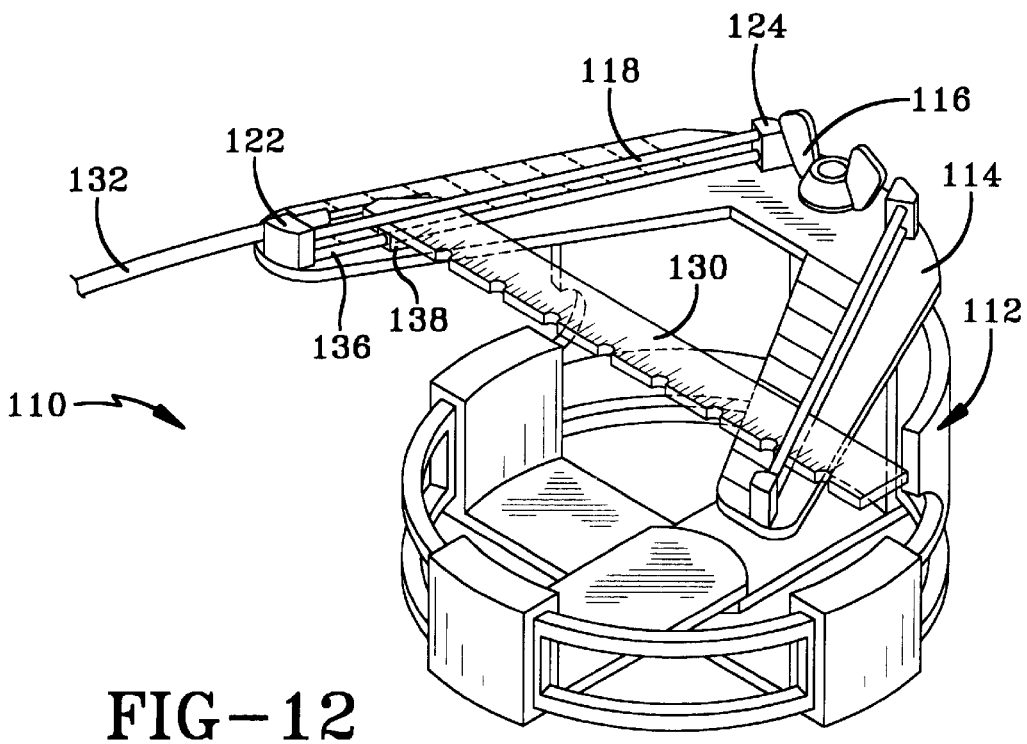
FIG. 12 is a perspective view of a stereotactic device that may be used in accordance with one embodiment of the present invention.

A preferred device also comprises a moveable member 130, preferably a transparent scaled member. The moveable member is preferably disposed between the first and second image-conspicuous lines 118, 120 and the upper plane portion 114, in a plane substantially parallel to the upper plane portion and having its ruled edge be substantially perpendicular to the angle bisector of the upper plane portion 114. As shown in FIG. 12, the moveable member 130 may be connected to the upper plane portion 114 by any appropriate means, but preferably by having an extension 138 adapted to surround and slide along a guide 136 on said upper plane portion 114. Referring again to FIG. 11, the moveable member is preferably adapted to move from the first end 122 to the second end 124 of the first line 118 at a rate equal to the movement from the first end 126 to the second end 128 of the second line 120, so as to have the ruled edge of the moveable member remain perpendicular to the angular bisector of the upper plane portion 114 angle. The moveable member may also have image-conspicuous gradations along its ruled edge. These gradations may be of any appropriate material, such as embedded wire or spots of barium ink or paste.

The moveable member 130 may also be adapted to slide from side to side within the device, always remaining sufficiently perpendicular to the angular bisector. In this respect, the moveable member 130 may have an aperture 152 (see FIGS. 15 and 16) through which at least a portion of a medical instrument may be passed. In this case, the medical instrument would not be inserted along a vector at a measured position along the ruled moveable member, but would pass through the aperture 152, the aperture 152 being moved to the appropriate vector point.

Figure 13:
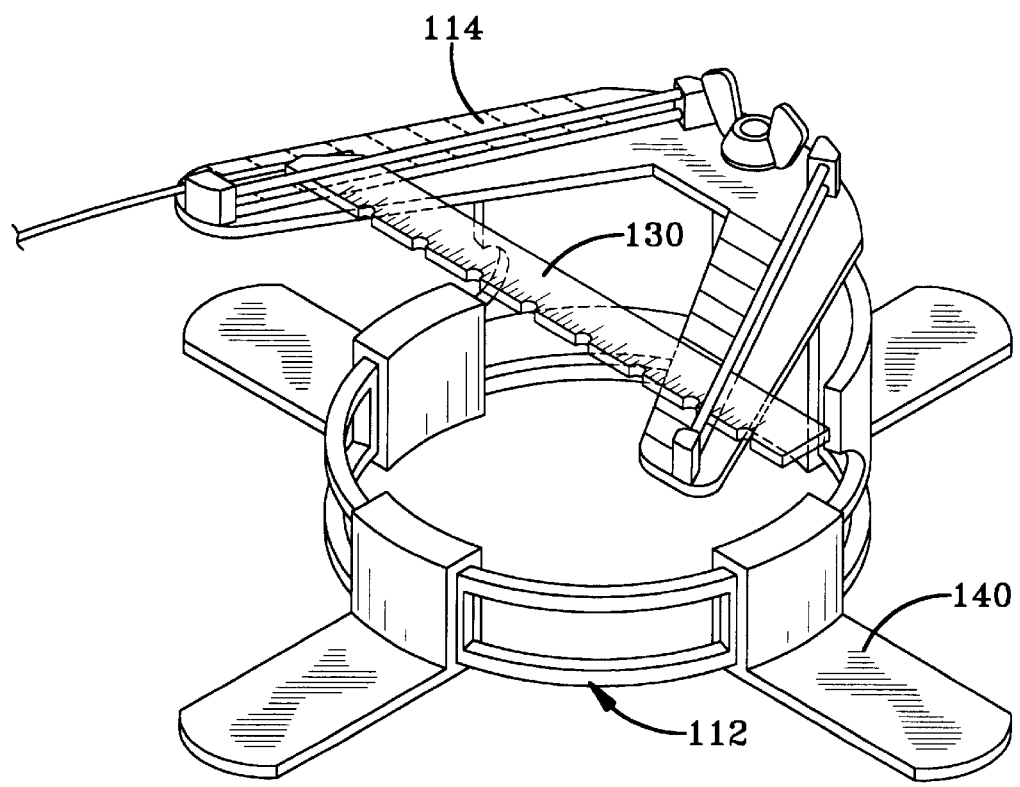
FIG. 13 is a front view stereotactic device that may be used in accordance with one embodiment of the present invention.

A device of the present invention also preferably has a remote actuator 132. The remote actuator may be a mechanical, electromechanical, hydraulic or other appropriate device. The actuator 132 preferably comprises a plastic cable surrounded by a plastic sheath, the plastic cable rigidly attached to the upper plane portion 114 and the plastic sheath rigidly connected to the moveable member 130 such that when the end of the sheath opposite the device is moved a fixed distance relative to the plastic cable, the moveable member moves the same distance relative to the frame 112. Any appropriate device may be attached the end of the cable and sheath opposite the device in order to move the moveable member a fixed distance, such as a threaded screw device or a sliding switch adapted to move in fixed increments. The extending portion of the remote actuator is preferably of a length to allow maximum travel distance for the moveable member. The remote actuators allow adjustment of the stereotactic device from a distance away from the device, thereby allowing an operator to avoid any radiation or other potential hazard at or near the stereotactic device during operation. Referring now to FIG. 13, the frame portion 112 may be attached to a patient by any appropriate means, such as by use of sterile adhesive strips 140 or an adhesive drape. There may also be a holding device, such as a foam ring, which may be placed on the person in order to hold the device in place when the device is positioned inside the ring.

Figure 14:
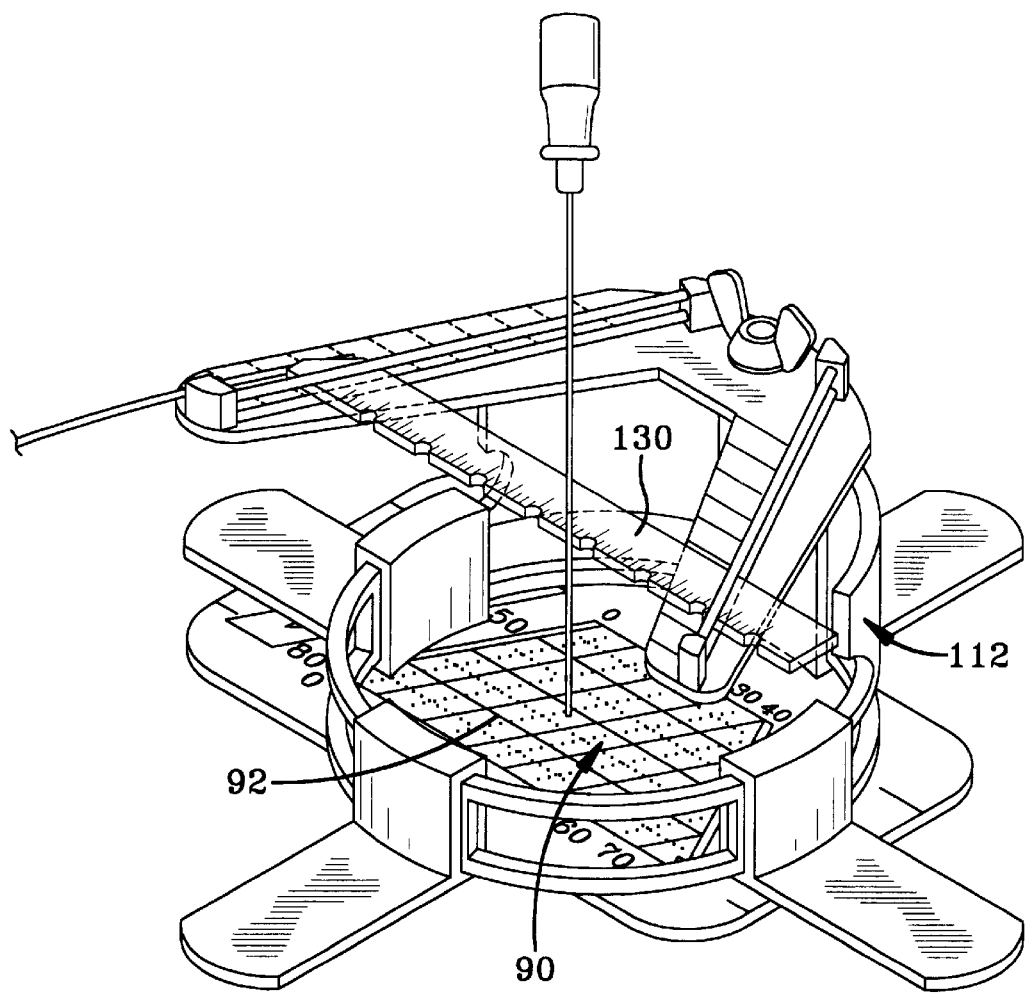
FIG. 14 is a perspective view of a remote-controlled stereotactic device, having a medical instrument inserted therethrough, that may be used in accordance with one embodiment of the present invention.

Referring to FIG. 14, the device preferably also utilizes a lower plane device 90, such as a sterile bandage, that may be placed upon a patient or target in order to locate an entry point. A preferred lower plane device 90 preferably includes image-conspicuous lines 92 and 93 (93 not shown in FIG. 14) such that MRI or CT imaging may be used to locate the entry position. The lines may be of any appropriate image-conspicuous material, such as tubes containing an image-conspicuous sterile fluid for MRI or wires coated in barium ink or paste for CT.

Referring to FIG. 14, once an entry point on the lower plane device 90 determined and the moveable member 130 positioned accordingly, a medical instrument 144 may be inserted into the target or patient along the vector defined by the entry point and the position along the moveable member. If the moveable member has an aperture as described above, the instrument would be passed along a vector through the aperture and the entry point.

Figure 15:
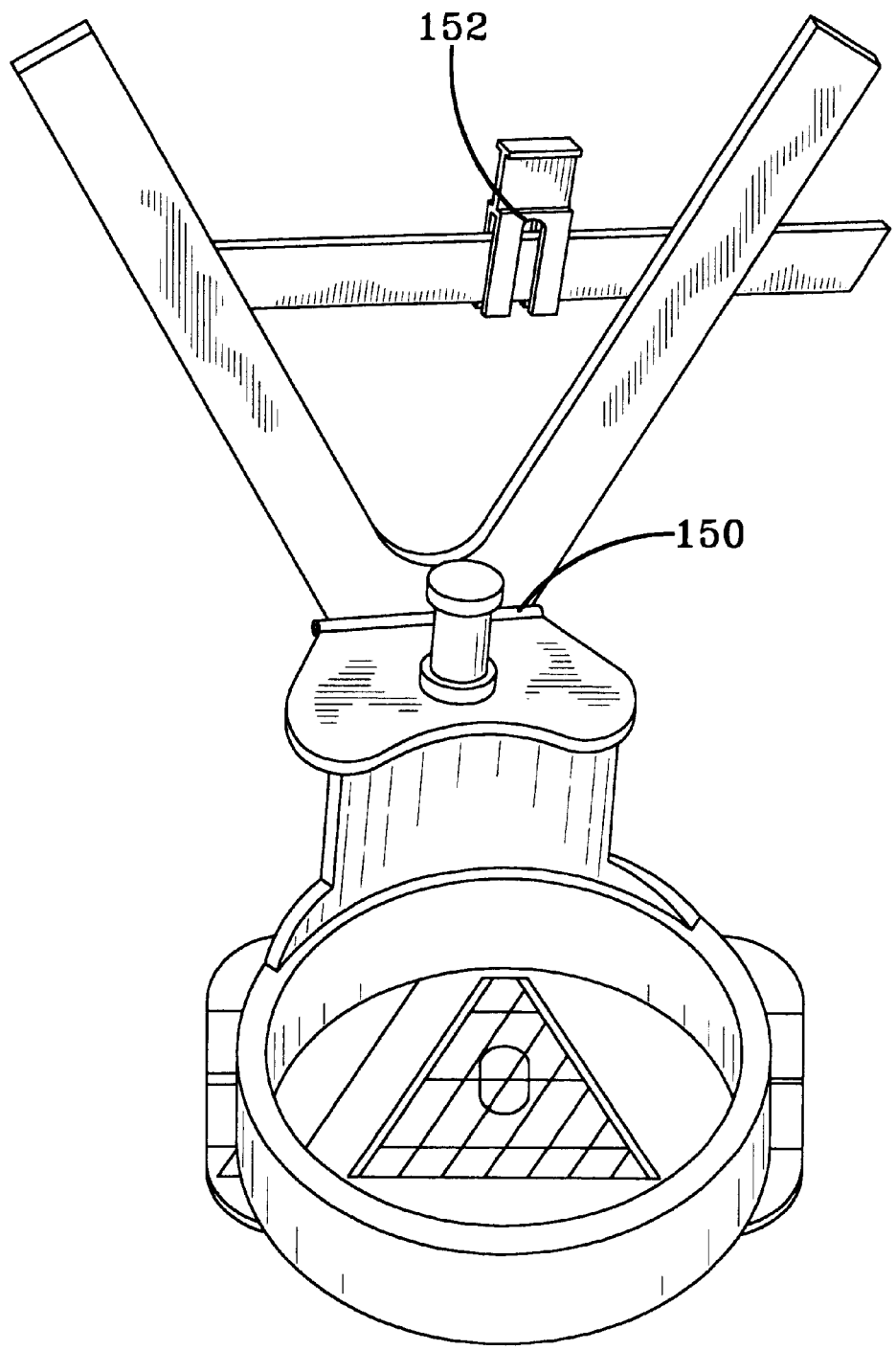
FIG. 15 shows an example of one embodiment of the present invention illustrating the use of a hinge to improve accessibility to the needle entry location.

Referring to FIG. 15, an optional hinge member 150 is shown so that the upper plane portion 114 may be moved out of the way to increase access to the underlying area. Also shown is an optional aperture 152 to assist in fixing the location of a medical device with respect to the upper plane.

Figure 16:
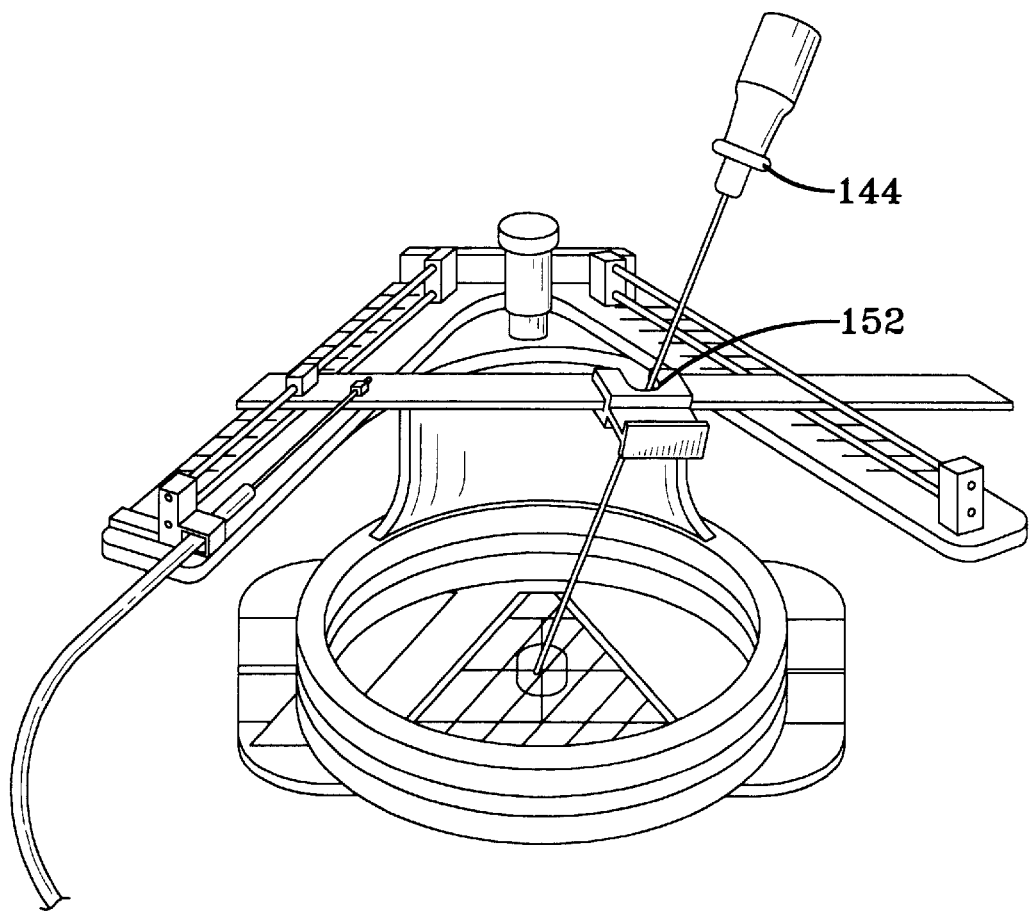
FIG. 16 shows an example of an aperture connected to the moveable member to assist in defining the entry vector in accordance with one embodiment of the present invention.

Referring to FIG. 16, shows a medical instrument 144 passing through aperture 152.

Figure 17:
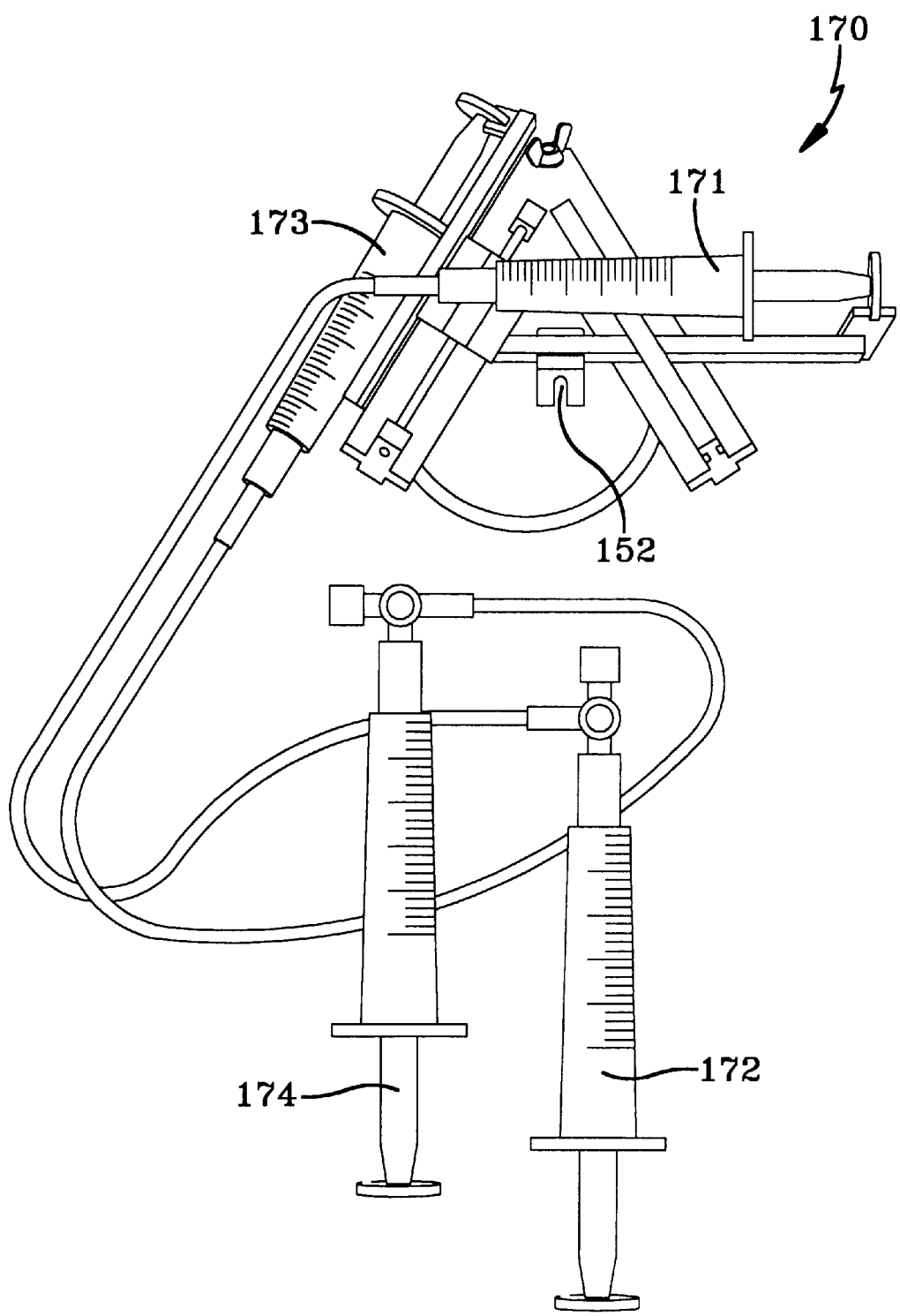
FIG. 17 shows an example of remote activators in accordance with one embodiment of the present invention.

Referring to FIG. 17, a remote control device 170 is shown adapted with remote actuators 171, 173 and corresponding controls 172, 174. The remote control device 170 is attached to the upper plane portion. With this remote control system, the operator is in hydraulic communication with the upper plane portion. Actuator 171 is adapted to change the position of aperture 152 along the moveable member 130. By moving control 172, a corresponding movement in actuator 171 is accomplished. Actuator 173 is adapted to change the position of moveable member 130. By moving control 174, a corresponding movement in moveable member 130 is accomplished. It should be noted that the remote control device 170 may comprise hydraulic, electrical, mechanical or other suitable means to effect the desired remote control operation of the device.

Figure 18:
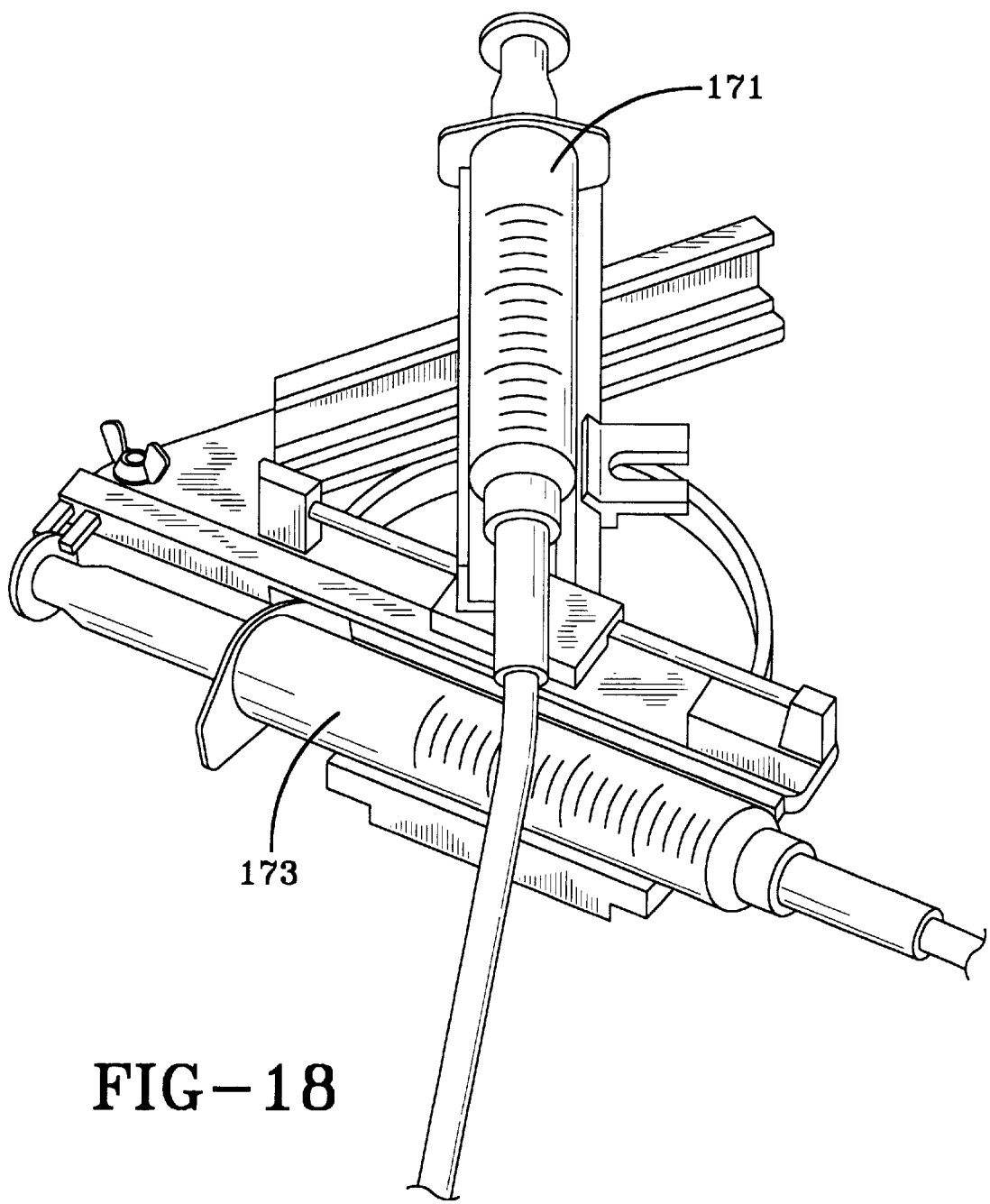
FIG. 18 shows a close-up view of the attachments of the remote activators on the stereotactic device in accordance with one embodiment of the present invention.

Referring to FIG. 18, the attachment of remote actuators 171 and 173 are shown in greater detail.

In order to operate a preferred device of the present invention, the following steps preferably may be followed for cross-sectional imaging procedures:

1. A non-sterile image-conspicuous pattern is placed on the skin of the patient at the estimated entry point location and the patient is imaged.
2. When the target is found on the image the precise entry point location may be localized on the pattern and the skin may be marked (ink) at the determined entry point. A line is also drawn on the skin parallel to the section plane for future alignment of the device.
3. The skin preferably is prepared for sterile handling and treatment.
4. The sterile skin entry point bandage having an image-conspicuous pattern is then centered on the skin over the predetermined skin entry mark. If the bandage is not transparent, an area of the bandage over the entry point may be cut out in order to provide access to the marked skin, or, alternatively, the bandage material can be punctured. When it is placed on the patient the sterile bandage can be located so that the ink marked skin entry point is aligned at a specific point on the device pattern grid that is convenient and easy for the operator to measure.

5. The skin may be numbed to anesthetize the chosen point of entry.

6. Using the laser localizing light of the imager if necessary, the portion of the device containing the frame and upper plane is then placed on the patient parallel to the image plane so that the chosen vector can be aligned with the target, the entry point, and the moveable member's range of motion.

7. An image is acquired to confirm correct alignment.

8. The vector to the target is drawn on the image extending from the target through the predetermined skin entry point.

9. The upper level device moveable member is then moved by remote control the correct dimension and direction to confirm that the needle is in the image plane and pointing at the target. If the moveable member has a moveable probe-holding aperture, the aperture is positioned at the indicated device location of alignment. If there is no moveable aperture, the correct position along the ruled moveable member is determined and used as the probe location.

10. The needle is advanced a short distance into the patient and then confirmed to be in the correct vector position by imaging and the distance to the target from the tip of the needle is measured.

11. The needle may then be advanced to the target using local anesthetic, if necessary.

12. The final needle position in the target is then confirmed by imaging and the upper level device components can be removed from the procedural field if desired at this time.

13. The procedure is completed in a standard fashion, i.e., through administration of medication to the target site by removal of tissue for biopsy.

14. After procedure completion the needle and the rest of the device components are removed as desired.

In another example of the device's application, it may be used in conjunction with radioscopy or fluoroscopy.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims, which are incorporated herein by reference.

What is claimed is:

1. A stereotactic system for determining a vector for inserting at least a portion of a medical device into a patient to contact a target located within said patient for use with imaging equipment, said stereotactic system comprising:

a. a lower plane portion defining a first plane, said lower plane portion comprising at least a first image-conspicuous line and a second image-conspicuous line, said first image-conspicuous line in non-parallel relation to said second image-conspicuous line so as to define an angle and an area between said at least first image-conspicuous line and said second image-conspicuous line, said lower plane portion adapted to be placed directly on said patient, said lower plane portion capable of being aligned with an image plane, said lower plane portion further adapted to permit passage of at least a portion of a medical device;

b. a frame, said frame capable of being mounted to said patient; and c. an upper plane portion defining a second plane, said upper plane portion attached to said frame, said frame adapted to support said upper plane portion above said lower plane portion such that said second plane is substantially parallel to said first plane, said upper plane portion further comprising at least a first image-conspicuous line and a second image-conspicuous line, said first image-conspicuous line in non-parallel relation to said second image-conspicuous line so as to define an angle and an area between said at least first image-conspicuous line and said second image-conspicuous line, said upper plane portion capable of being aligned with said image plane, said upper plane portion further adapted to permit passage of at least a portion of a medical device.

2. A stereotactic system of claim 1, further comprising at least one offset line, each said at least one offset line disposed in said area between said first image-conspicuous line and said second image-conspicuous line, each said at least one offset line in parallel relationship with said first image conspicuous line, each said at least one offset line capable of providing a distance of said vector from said first image-conspicuous line along said image plane.

3. A stereotactic system of claim 1, wherein said upper plane portion further comprises a moveable member having at least one edge, said moveable member disposed between said first image-conspicuous line and said second image conspicuous line, said moveable member adapted to move in a plane parallel to said upper plane portion and normal to said image plane, said moveable member capable of providing a position relative to said first image-conspicuous line along said image plane.

4. A stereotactic system of claim 3, wherein said moveable member further comprises at least one image-conspicuous marker disposed along at least one edge of said moveable member, said at least one image-conspicuous marker capable of being moved by said moveable member into said image plane for assistance in determining said position relative to said first image-conspicuous line along said image plane.

5. A stereotactic system according to claim 4 wherein said moveable member is in communication with at least one remote control device.

6. A stereotactic system according to claim 4, further comprising an aperture, said aperture having an orifice capable of permitting at least a portion of said medical device to pass therethrough, said aperture mounted on said at least one edge of said moveable member, said aperture capable of sliding along said at least one edge parallel to said image plane.

7. A stereotactic system according to claim 1, further comprising a hinge, said hinge fixedly attached to said frame and to said upper plane portion, said hinge permitting said upper plane portion to move relative to said frame portion.

8. A stereotactic system according to claim 1, wherein said image-conspicuous lines are constructed from a material selected from the group consisting of: metal, barium paste, or barium ink.

9. A stereotactic system according to claim 1, wherein said angle is greater that about 35 degrees.

10. A stereotactic system according to claim 1, wherein said angle is 53 degrees.

11. A stereotactic system according to claim 1, further comprising a disposable lower plane portion, said disposable lower plane portion comprising at least a first image-conspicuous line and a second image-conspicuous line, said first image-conspicuous line in non-parallel relation to said second image-conspicuous line so as to define an angle and an area between said at least first image-conspicuous line and said second image-conspicuous line, said disposable lower plane portion adapted to be placed directly on said patient, said disposable lower plane portion capable of being aligned with an image plane.

12. A stereotactic system of claim 1, wherein said upper plane portion further comprises a membrane, said membrane occupying said area between said at least first image-conspicuous line and said second image-conspicuous line, said membrane capable of being pierced by at least a portion of a medical device.

13. A stereotactic system of claim 12, wherein said membrane is transparent.

14. A stereotactic system of claim 1, wherein said upper plane portion further comprises a membrane with at least one hole, said membrane occupying said area between said at least first image-conspicuous line and said second image-conspicuous line, said at least one hole adapted to permit passage of at least a portion of a medical device.

15. A method of using a stereotactic system for determining a vector for inserting at least a portion of a medical device into a patient to contact a target located within said patient, for use with imaging equipment, said method comprising:
   a. placing a lower plane portion on the surface of a patient in alignment with an image plane, said lower plane portion defining a first plane, said lower plane portion comprising at least a first image-conspicuous line and a second image-conspicuous line, said first image-conspicuous line in non-parallel relation to said second image-conspicuous line so as to define an angle and an area between said at least first image-conspicuous line and said second image-conspicuous line, said lower plane portion further adapted to permit passage of at least a portion of a medical device;
   b. taking at least a first image to locate said target within said patient, said at least first image containing a first image-mark created by said first image-conspicuous line and a second image-mark created by said second image-conspicuous line;
   c. drawing a line on said first image from said target through said area defined by said first image-mark and said second image-mark so as to define a vector and a skin entry point;
   d. preparing said surface of said patient in a region about said skin entry point for sterile handling;
   e. placing and temporarily attaching a frame on said patient, said frame connected to an upper plane portion defining a second plane, said upper plane portion attached to said frame, said frame adapted to support said upper plane portion above said lower plane portion such that said second plane is substantially parallel to said first plane, said upper plane portion further comprising at least a first image-conspicuous line and a second image-conspicuous line, said first image-conspicuous line in non-parallel relation to said second image-conspicuous line so as to define an angle and an area between said at least first image-conspicuous line and said second image-conspicuous line, said upper plane portion capable of being aligned with said image plane, said upper plane portion further adapted to permit passage of at least a portion of a medical device;
   f. taking at least a second image to confirm said vector, said at least second image containing a first upper image-mark created by said first image-conspicuous line of said upper plane portion and a second upper image-mark created by said second image-conspicuous line of said upper plane portion; and
   g. confirming said vector by drawing a line on said second image from said target through said skin entry point and through said area defined by said first upper image-mark and said second upper image-mark.

16. A method of using a stereotactic system for determining a vector for inserting at least a portion of a medical device into a patient to contact a target located within said patient, for use with imaging equipment, said method comprising:
   a. placing a disposable lower plane portion on the surface of a patient in alignment with an image plane, said disposable lower plane portion defining a first plane, said disposable lower plane portion comprising at least a first disposable image-conspicuous line and a second disposable image-conspicuous line, said first disposable image-conspicuous line in non-parallel relation to said second disposable image-conspicuous line so as to define an angle and an area between said at least first disposable image-conspicuous line and said second disposable image-conspicuous line;
   b. taking at least a first image to locate said target within said patient, said at least first image containing a first image-mark created by said first disposable image-conspicuous line and a second disposable image-mark created by said second disposable image-conspicuous line;
   c. drawing a line on said at least first image from said target through said area defined by said first disposable image-mark and said second disposable image-mark so as to define a vector and a skin entry point;
   d. placing a mark on said surface of said patient at said skin entry mark;
   e. replacing said disposable lower plane portion with a lower plane portion on said surface of said patient, said lower plane portion in alignment with said image plane, said lower plane portion defining a second plane, said lower plane portion comprising at least a first image-conspicuous line and a second image-conspicuous line, said first image-conspicuous line in non-parallel relation to said second image-conspicuous line so as to define an angle and an area between said at least first image-conspicuous line and said second image-conspicuous line, said lower plane portion positioned so as to contain said skin entry mark at a known position in said area, said lower plane portion further adapted to permit passage of at least a portion of a medical device;
   f. taking at least a second image to locate said target within said patient, said at least second image containing a first image-mark created by said first image-conspicuous line and a second image-mark created by said second image-conspicuous line;
   g. confirming said vector by drawing a line on said at least second image from said target through said known position of said skin entry point in said area defined by said first image-mark and said second image-mark so as to define a vector and a skin entry point;
   h. placing a frame on said patient, said frame connected to an upper plane portion defining a third plane, said upper plane portion attached to said frame, said frame adapted to support said upper plane portion above said lower plane portion such that said third plane is substantially parallel to said second plane, said upper plane portion further comprising at least a first image-conspicuous line and a second image-conspicuous line, said first image-conspicuous line in non-parallel relation to said second image-conspicuous line so as to define an angle and an area between said at least first image-conspicuous line and said second image-conspicuous line, said upper plane portion capable of being aligned with said image plane, said upper plane portion further adapted to permit passage of at least a portion of a medical device, i. aligning said upper plane portion with said image plane;
j. taking at least a third image to confirm said vector, said at least third image containing a first upper image-mark created by said first image-conspicuous line of said upper plane portion and a second upper image-mark created by said second image-conspicuous line of said upper plane portion; and
k. confirming said vector by drawing a line on said third image from said target through said skin entry point and through said area defined by said first upper image-mark and said second upper image-mark.

17. A method according to claim 15, further comprising the additional step of sterilizing an area of said surface of said patient about said skin entry point.

18. A method according to claim 16, further comprising the additional step of sterilizing an area of said surface of said patient about said skin entry point.

19. A method according to claim 16, wherein said disposable lower plane portion is capable of being pierced by a marking instrument so as to permit identification of a skin entry point of said surface of said patient.

* * * * *